United States Patent [19]

Sipos et al.

[11] 4,041,232

[45] Aug. 9, 1977

[54] AMPHOTERICIN B METHYL ESTER SALTS

[75] Inventors: Frank Sipos, Princeton; Adam J. Keseleski, Edison, both of N.J.

[73] Assignee: E. R. Squibb & Sons, Inc., Princeton, N.J.

[21] Appl. No.: 660,598

[22] Filed: Feb. 23, 1976

[51] Int. Cl.² .............................................. C07H 17/08
[52] U.S. Cl. ...................................... 536/17; 424/180;
536/4; 536/18; 536/115
[58] Field of Search ...................................... 536/17, 4

[56] References Cited

U.S. PATENT DOCUMENTS 3,945,993   3/1976   Schaffner et al. ...................... 536/17

*Primary Examiner*—Johnnie R. Brown
*Attorney, Agent, or Firm*—Lawrence S. Levinson; Merle J. Smith; Burton Rodney

[57] ABSTRACT

Amphotericin B methyl ester salts, such as salts formed by reaction with mono and dicarboxylic amino acids (such as aspartic acid, or glutamic acid or pyroglutamic acid), hydroxy carboxylic acids (such as lactic acid) and mono and dicarboxylic acids (such as acetic acid) are provided and have been found to be readily water-soluble and at least as stable and active as the parent ester compound.

10 Claims, No Drawings

AMPHOTERICIN B METHYL ESTER SALTS

The present invention relates to water-soluble salts of the methyl ester of amphotericin B.

The methyl ester of amphotericin B which has the formula

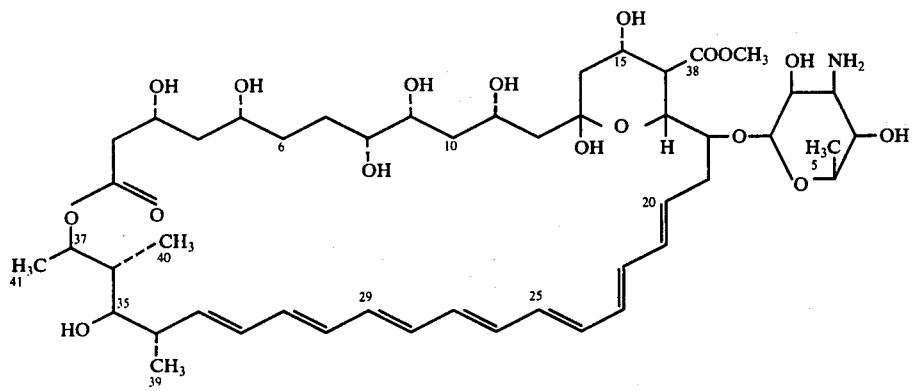

$C_{48}H_{74}NO_{17}$ has been prepared by mixing amphotericin B starting material with dimethylsulfoxide and methanol to form a solution of the amphotericin B. The dissolved amphotericin B is then esterified by reaction with diazomethane and the resulting reaction mixture treated with ethyl ether to precipitate the methyl ester.

While the methyl ester of amphotericin B is particularly valuable for its antifungal properties and in the apparent inability of fungus organisms to develop strains or forms that are resistant to amphotericin B methyl ester, its use has been limited by lack of adequate water solubility.

The present invention provides new more soluble forms of the methyl ester of amphotericin B which are salts thereof formed by reaction with monocarboxylic amino acids, dicarboxylic amino acids, hydroxy acids, hydrocarbon monocarboxylic acids and hydrocarbon polycarboxylic acids.

The mono and dicarboxylic amino acids (natural or synthetic) which are suitable for use herein include alanine, arginine, asparagine, aspartic acid, cysteine, glutamic acid, glutamine, glycine, histidine, isoleucine, leucine, lysine, methionine, phenylalanine, proline, sarcosine, serine, threonine, tryptophan, tyrosine and valine and all optical isomers and derivatives thereof, with glutamic acid, aspartic acid and pyroglutamic acid being preferred.

The hydroxy acids suitable for use herein may contain one or two hydroxy groups and up to 12 carbons, and include, but are not limited to, glycolic acid, lactic acid, hydroxybutyric acid, malic acid, and tartaric acid, including isomers thereof, with lactic acid being preferred.

The hydrocarbon mono and dicarboxylic acid may contain one, two or three carboxyl groups and (up to 15 carbons and) include alkanoic acids, alkenoic acids or aromatic acids. Such acids suitable for use herein include, but are not limited to, formic acid, acetic acid, butyric acid, valeric acid, caproic acid, caprylic acid, capric acid, octanoic acid, palmitic acid, stearic acid, glutaric acid, adipic acid, malonic acid, succinic acid, oxalic acid, crotonic acid, oleic acid, acrylic acid, vinylacetic acid, maleic acid, fumaric acid, benzoic acid, phenylacetic acid, hydrocinnamic acid, cinnamic acid, mellitic acid, o- or p-toluic acid, phthalic acid, terephthalic acid or naphthoic acids, with acetic acid being preferred.

Preferred salts of the amphotericin B methyl ester in accordance with the present invention include the glutamic acid salt, pyroglutamic acid salt, aspartic acid salt, and the acetic acid salt.

In general, aqueous solutions containing from 0.1 to 10% by weight of the salts of the invention will have a pH within the range of from about 5 to about 6.5 and preferably from about 6 to about 6.4.

The salts of the invention are readily water soluble, that is, have a solubility of 10% or more, and are as stable as and may be more stable than, and as active as the methyl ester of amphotericin B.

The salts of the invention may be easily prepared by simply adding portions of the amphotericin B methyl ester to an aqueous solution or suspension of the particular acid (0.2 to 2% by weight acid) to be employed. Where the acid is a mono carboxylic acid, it is preferred that 1:1 molar ratios of the acid and ester be employed. However, where dicarboxylic acids are employed, it is preferred that a weight ratio of acid:ester of within the range of from about 1:1 to about 1:2 and more preferably 1:2 be employed.

The salts of the invention retain the antifungal activity of amphotericin B methyl ester, are stable in the dry form as well as in solution, and are readily soluble in water so as to permit the preparation of concentrated aqueous solutions in the range of from about 2 g to 12 g per liter. Such concentrated aqueous solutions may be used, for example, to control fungal growths in the digestive tract of fowl by supplying it to the drinking water.

The following Examples represent preferred embodiments of the present invention.

EXAMPLE 1

Amphotericin B Methyl Ester-L-Glutamate

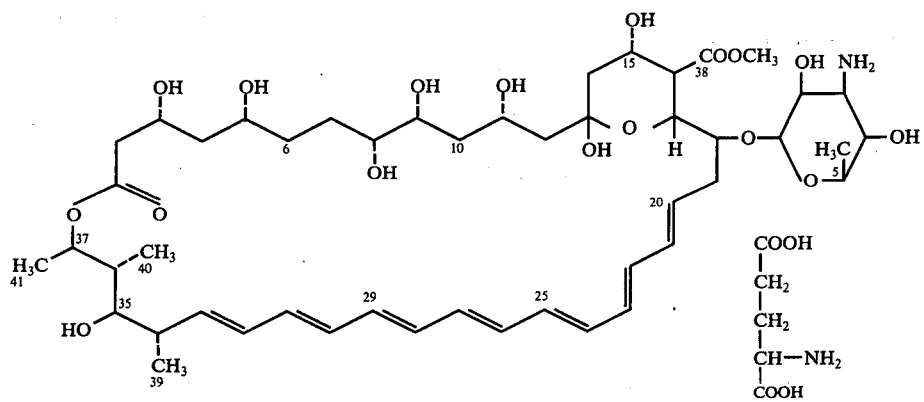

AMPHOTERICIN B METHYL ESTER GLUTAMATE (SALT)

$C_{53}H_{83}N_2O_{21}$ (M.W. = 1084.2)

Amphotericin B methyl ester (9.36 g 0.01 Mol) is added in portions to a suspension of the L-glutamic acid (1.47 g 0.01 Mole) in 300 ml of water and the mixture is stirred until complete dissolution. The clear solution is thereafter freeze dried. The yield is quantitative. The product has a solubility in water of about 10% or more at RT.

EXAMPLE 2

Amphotericin B Methyl Ester-Pyroglutamate

Amphotericin B methyl ester (9.36 g 0.01 Mol) is added in portions to a solution of pyroglutamic acid (1.30 g, 0.01 Mol) in 500 ml of water and stirred until dissolution (5–10 minutes). The clear solution is thereafter lyopholized. The resulting product is found to be very soluble in water (more than 10% soluble at RT).

EXAMPLE 3

Amphotericin B Methyl Ester-L-Glutamate

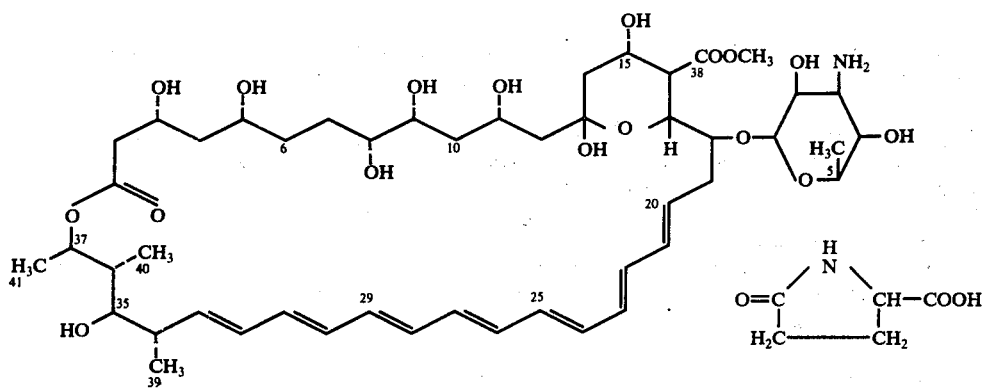

AMPHOTERICIN B METHYL ESTER-PYROGLUTAMATE (SALT)

$C_{53}H_{80}N_2O_{20}$ (M.W. = 1065.2)

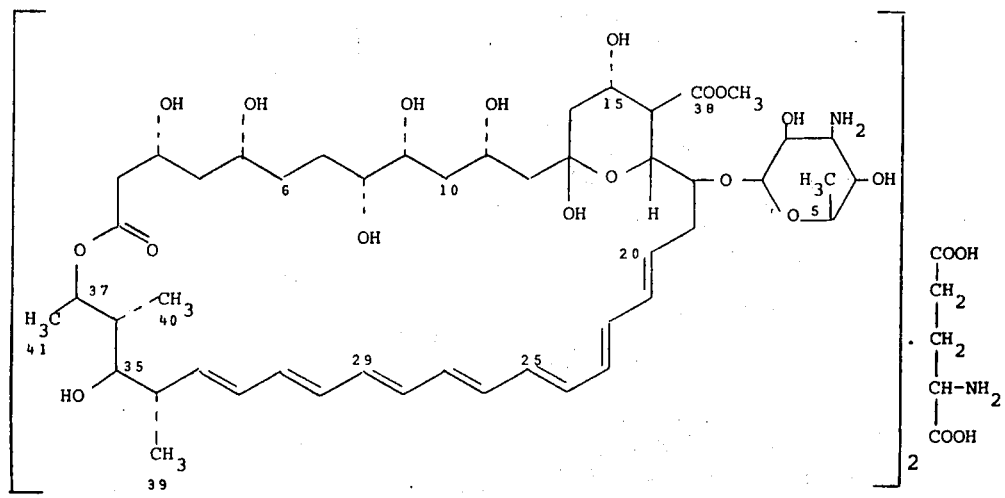

DI-[AMPHOTERICIN B METHYL ESTER] GLUTAMATE (SALT)

$C_{101}H_{157}N_3O_{38}$ (M.W. = 2021.4)

Amphotericin B methyl ester (9.36 g, 0.01 Mol) is added in portions to a solution of L-glutamic acid (0.81 g, 0.0055 Mol) in 500 ml of water and stirred until complete dissolution (1 hour). The clear solution is then lyopholized. The yield is 88.9%. The product is soluble in water even at concentrations of 10% at RT and when dissolved in water to form a 1% solution is found to have a pH of 6.02.

EXAMPLE 4

Amphotericin B Methyl Ester-L-Aspartate

Amphotericin B methyl ester (9.36 g, 0.01 Mol) is added in portions to a solution of L-aspartic acid (0.73 g, 0.0055 Mol) in 500 ml of water and stirred until dissolution (1 hour). The clear solution is thereafter freeze-dried. The product when dissolved in water (1%) has a pH of 6.25 and a solubility of greater than 10% at RT.

EXAMPLE 5

Amphotericin B Methyl Ester-L-Aspartate

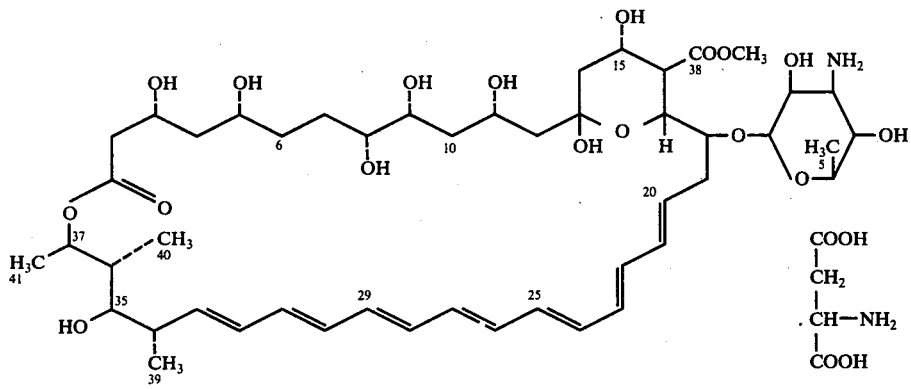

AMPHOTERICIN B METHYL ESTER ASPARTATE (SALT)
$C_{52}H_{81}N_2O_{21}$ (M.W. = 1072.2)

Amphotericin B methyl ester (9.36 g, 0.01 Mol) is added in portions to a solution of L-aspartic acid (1.33 g, 0.01 Mol) in 500 ml of water and stirred until complete dissolution. The clear solution is then lyopholized. The product has a solubility of more than 10% water at RT.

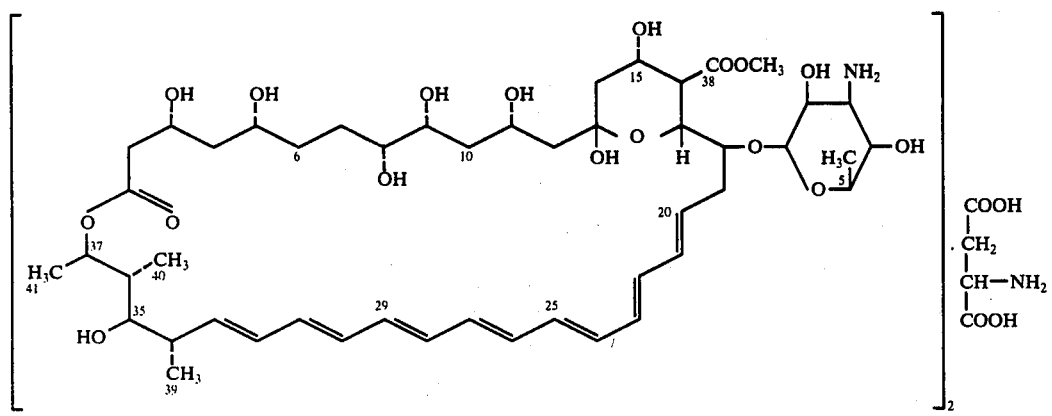

DI-[AMPHOTERICIN B METHYL ESTER] ASPARTATE (SALT)

$C_{100}H_{155}N_3O_{38}$ (M.W. = 2007.36)

EXAMPLE 6

Amphotericin B Methyl Ester Acetate

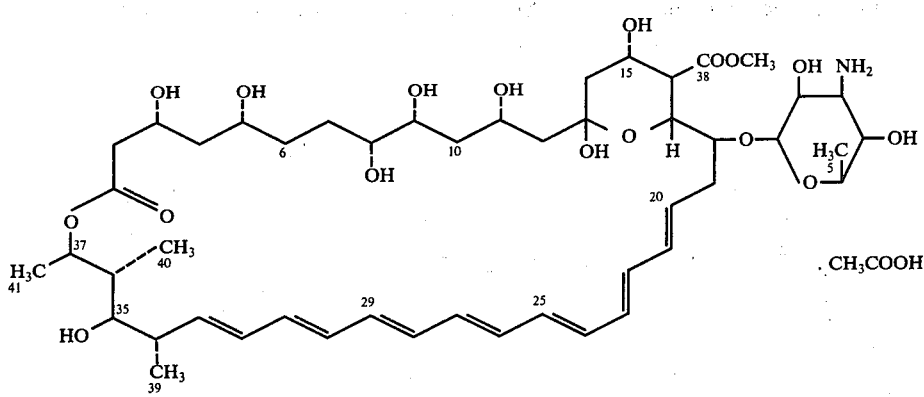

AMPHOTERICIN B METHYL ESTER ACETATE (SALT)
$C_{50}H_{78}NO_{19}$ (M.W. = 1011.2)

Amphotericin B methyl ester (9.36 g, 0.01 Mol) is added in portions to a solution of acetic acid (0.60 g, 0.01 Mol) in 500 ml of water and stirred until complete dissolution. The clear solution is then lyopholized. The product when dissolved in water (1%) has a pH of 6.4 and a solubility greater than 10% at R.T.

EXAMPLE 7

Amphotericin B Methyl Ester Propionate

Amphotericin B methyl ester is added in portions to a solution of propionic acid in 1:1 molar ratio in water and stirred until dissolution. The clear solution is then lyopholized.

EXAMPLE 8

Amphotericin B Methyl Ester Octanoate

Amphotericin B methyl ester is added in portions to a solution of octanoic acid in 1:1 molar ratio in water and stirred until dissolution. The clear solution is then lyopholized.

EXAMPLE 9

Amphotericin B Methyl Ester Laurate

Amphotericin B methyl ester is added in portions to a solution of lauric acid in 1:1 molar ratio in water and stirred until dissolution. The clear solution is then lyopholized.

EXAMPLE 10

Amphotericin B Methyl Ester Formate

Amphotericin B methyl ester is added in portions to a solution of formic acid in 1:1 molar ratio in water and stirred until dissolution. The clear solution is then lyopholized.

EXAMPLE 11

Amphotericin B Methyl Ester Lactate

Amphotericin B methyl ester is added in portions to a solution of lactic acid in 1:1 molar ratio in water and stirred until dissolution. The clear solution is then lyopholized.

EXAMPLE 12

Amphotericin B Methyl Ester Alaninate

Amphotericin B methyl ester is added in portions to a solution of alanine in 1:1 molar ratio in water and stirred until dissolution. The clear solution is then lyopholized.

EXAMPLE 13

Amphotericin B Methyl Ester Carbamate

Amphotericin B methyl ester is added in portions to a solution of carbamic acid in 1:1 molar ratio in water and stirred until dissolution. The clear solution is then lyopholized.

EXAMPLE 14

Amphotericin B Methyl Ester Glycinate

Amphotericin B methyl ester is added in portions to a solution of glycine in 1:1 molar ratio in water and stirred until dissolution. The clear solution is then lyopholized.

EXAMPLE 15

Amphotericin B Methyl Ester Sarcosinate

Amphotericin B methyl ester is added in portions to a solution of sarcosine in 1:1 molar ratio in water and stirred until dissolution. The clear solution is then lyopholized.

EXAMPLE 16

Amphotericin B Methyl Ester Valinate

Amphotericin B methyl ester is added in portions to a solution of valine in 1:1 molar ratio in water and stirred until dissolution. The clear solution is then lyopholized.

EXAMPLE 17

Amphotericin B Methyl Ester Leucinate

Amphotericin B methyl ester is added in portions to a solution of leucine in 1:1 molar ratio in water and stirred until dissolution. The clear solution is then lyopholized.

EXAMPLE 18

Amphotericin B Methyl Ester Isovalinate

Amphotericin B methyl ester is added in portions to a solution of isovaline in 1:1 molar ratio in water and stirred until dissolution. The clear solution is then lyopholized.

EXAMPLE 19

Amphotericin B Methyl Ester Phenylalaninate

Amphotericin B methyl ester is added in portions to a solution of phenylalanine in 1:1 molar ratio in water and stirred until dissolution. The clear solution is then lyopholized.

EXAMPLE 20

Amphotericin B Methyl ESter Serinate

Amphotericin B methyl ester is added in portions to a solution of serine in 1:1 molar ratio in water and stirred until dissolution. The clear solution is then lyopholized.

EXAMPLE 21

Amphotericin B Methyl Ester Cysteinate

Amphotericin B methyl ester is added in portions to a solution of cysteine in 1:1 molar ratio in water and stirred until dissolution. The clear solution is then lyopholized.

EXAMPLE 22

Amphotericin B Methyl Ester Methioninate

Amphotericin B methyl ester is added in portions to a solution of methioine in 1:1 molar ratio in water and stirred until dissolution. The clear solution is then lyopholized.

EXAMPLE 23

Amphotericin B Methyl Ester Lysinate

Amphotericin B methyl ester is added in portions to a solution of lysine in 1:1 molar ratio in water and stirred until dissolution. The clear solution is then lyopholized.

EXAMPLE 24

Amphotericin B Methyl Ester Ornithinate

Amphotericin B methyl ester is added in portions to a solution of ornithine in 1:1 molar ratio in water and stirred until dissolution. The clear solution is then lyopholized.

EXAMPLE 25

Amphotericin B Methyl Ester Asparaginate

Amphotericin B methyl ester is added in portions to a solution of asparagine in 1:1 molar ratio in water and stirred until dissolution. The clear solution is then lyopholized.

EXAMPLE 26

Amphotericin B Methyl Ester Histidinate

Amphotericin B methyl ester in added in portions to a solution of histidine in 1:1 molar ratio in water and stirred until dissolution. The clear solution is then lyopholized.

EXAMPLE 27

Amphotericin B Methyl Ester Tryptophanate

Amphotericin B methyl ester is added in portions to a solution of tryptophan in 1:1 molar ratio in water and stirred until dissolution. The clear solution is then lyopholized.

EXAMPLE 28

Amphotericin B Methyl Ester Prolinate

Amphotericin B methy ester is added in portions to a solution of proline in 1:1 molar ratio in water and stirred until dissolution. The clear solution is then lyopholized.

EXAMPLE 29

Amphotericin B Methyl Ester Hydroxyprolinate

Amphotericin B methyl ester is added in portions to a solution of hydroxyproline in 1:1 molar ratio in water and stirred until dissolution. The clear solution is then lyopholized.

EXAMPLE 30

Amphotericin B Methyl Ester Threoninate

Amphotericin B methyl ester is added in portions to a solution of threonine 1:1 molar ratio in water and stirred until dissolution. The clear solution is then lyopholized.

EXAMPLE 31

Amphotericin B Methyl Ester Isoleucinate

Amphotericin B methyl ester is added in portions to a solution of isoleucine in 1:1 molar ratio in water and stirred until dissolution. The clear solution is then lyopholized.

EXAMPLE 32

Amphotericin B Methyl Ester Norleucinate

Amphotericin B methyl ester is added in portions to a solution of norleucine in 1:1 molar ratio in water and stirred until dissolution. The clear solution is then lyopholized.

EXAMPLE 33

Amphotericin B Methyl Ester Norvalinate

Amphotericin B methyl ester is added in portions to a solution or norvaline in 1:1 molar ratio of water and stirred until dissolution. The clear solution is then lyopholized.

EXAMPLE 34

Amphotericin B Methyl Ester Tartrate

Amphotericin B methyl ester is added in portions to a solution of tartaric acid in 1:1 molar ratio in water and stirred until dissolution. The clear solution is then lyopholized.

EXAMPLE 35

Amphotericin B Methyl Ester Valerate

Amphotericin B methyl ester is added in portions to a solution of valeric acid in 1:1 molar ratio in water and stirred until dissolution. The clear solution is then lyopholized.

EXAMPLE 36

Amphotericin B Methyl Ester Glutarate

Amphotericin B methyl ester is added in portions to a solution of glutaric acid in 2:1 molar ratio in water and stirred until dissolution. The clear solution is then lyopholized.

EXAMPLE 37

Amphotericin B Methyl Ester Adipate

Amphotericin B methyl ester is added in portions to a solution of adipic acid in 2:1 molar ratio in water and stirred until dissolution. The clear solution is then lyopholized.

EXAMPLE 38

Amphotericin B Methyl Ester Malonate

Amphotericin B methyl ester is added in portions to a solution of malonic acid in 2:1 molar ratio in water and stirred until dissolution. The clear solution is then lyopholized.

EXAMPLE 39

Amphotericin B Methyl Ester Succinate

Amphotericin B methyl ester is added in portions to a solution of succinic acid in 2:1 molar ratio in water and stirred until dissolution. The clear solution is then lyopholized.

EXAMPLE 40

Amphotericin B Methyl Ester Oxalate

Amphotericin B methyl ester is added in portions to a solution of oxalic acid in 2:1 molar ratio in water and stirred until dissolution. The clear solution is then lyopholized.

What is claimed is:

1. A salt of the methyl ester of amphotericin B, said salt being selected from mono and dicarboxylic amino acid salts of the methyl ester of amphotericin B.
2. The salt as defined in claim 1 wherein said salt is a salt of a monocarboxylic amino acid.
3. The salt as defined in claim 2 wherein said monocarboxylic amino acid is selected from the group consisting of carbamic acid, glycine, glycin, alanine, valine, leucine, isovaline, phenylalanine, tyrosine, sarcosine, serine, cysteine, methionine, norvaline, norleucine, isoleucine, threonine, thyroxine, arginine, lysine, ornithine, asparagine, citrulline, histidine, tryptophan, proline and hydroxyproline.
4. The salt as defined in claim 3 wherein said amino acid is pyroglutamic acid.
5. The salt as defined in claim 1 wherein said salt is a salt of a dicarboxylic amino acid.
6. The salt as defined in claim 5 wherein said amino acid is selected from the group consisting of glutamic acid and aspartic acid.
7. The salt as defined in claim 1 having the name amphotericin B methyl ester glutamate.
8. The salt as defined in claim 1 having the name amphotericin B methyl ester aspartate.
9. The salt as defined in claim 1 having the name amphotericin B methyl ester pyroglutamate.
10. The salt as defined in claim 1 having a pH when dissolved in water at 1% concentration ranging from about 5 to about 6.5.

* * * * *